US00PP36979P2

(12) United States Plant Patent
Farrow

(10) Patent No.: US PP36,979 P2
(45) Date of Patent: Sep. 23, 2025

(54) ***CAMELLIA* PLANT NAMED 'FARROWCJPD'**

(50) Latin Name: ***Camellia* hybrid**
Varietal Denomination: FARROWCJPD

(71) Applicant: Spring Meadow Nursery, Grand Haven, MI (US)

(72) Inventor: Michael W. Farrow, Warwick, MD (US)

(73) Assignee: Spring Meadow Nursery Inc., Grand Haven, MI (US)

( * ) Notice: Subject to any disclaimer, the term of this patent is extended or adjusted under 35 U.S.C. 154(b) by 0 days.

(21) Appl. No.: 18/978,379

(22) Filed: Dec. 12, 2024

(51) Int. Cl.
*A01H 5/00* (2018.01)
*A01H 6/00* (2018.01)

(52) U.S. Cl.
USPC ..... Plt./243

(58) Field of Classification Search
USPC ..... Plt./243
See application file for complete search history.

*Primary Examiner* — Susan McCormick Ewoldt
(74) *Attorney, Agent, or Firm* — Cassandra Bright

(57) ABSTRACT

A new and distinct cultivar of *Camellia* plant named 'FARROWCJPD' is disclosed, characterized by abundant fully double, soft pink flowers, and glossy, dark green foliage with a dark red flush. Plants are upright and well-branched, with good container performance. The new cultivar is a *Camellia*, suitable for ornamental garden purposes.

3 Drawing Sheets

Latin name of the genus and species: *Camellia* hybrid.
Cultivar denomination: 'FARROWCJPD'.

BACKGROUND OF THE INVENTION

The new cultivar is a product of a planned breeding program by the inventor. The open-pollination resulting in the new cultivar was made during the fall of 2017, at a nursery in Warwick, Maryland. The seed parent is the unpatented cultivar *Camellia* 'Winter's Joy'. The pollen parent is unidentified. The inventor discovered this new cultivar at the same nursery during the summer of 2018.

After identifying the new cultivar as a potentially interesting selection, the inventor first propagated plants of 'FARROWCJPD' by hardwood vegetative cuttings during the fall of 2019 at the same nursery in Warwick, Maryland. Multiple generations have been reproduced and have shown that the unique features of this cultivar are stable and reproduced true to type.

SUMMARY OF THE INVENTION

The cultivar 'FARROWCJPD' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'FARROWCJPD' These characteristics in combination distinguish 'FARROWCJPD' as a new and distinct *Camellia* cultivar:

1. Double, soft pink flowers.
2. Highly floriferous.
3. Hardiness USDA 7 (6b)-9.
4. Attractive, healthy, glossy, dark green foliage with a dark red flush.
5. Upright, well-branched habit which lends itself to good container performance.

COMPARISON TO PARENT CULTIVAR

'FARROWCJPD' is similar in most horticultural characteristics to the seed parent cultivar *Camellia* 'Winter's Joy'. Plants of the new cultivar 'FARROWCJPD' however, differ in the following:

1. Flower color of the new cultivar is a lighter pink than the flower color of the seed parent.
2. Plants of the new cultivar have a tighter, more well-branched habit, while plants of the seed parent have a looser, rangier habit.
3. Plants of the new cultivar have a longer flowering period than plants of the seed parent.

COMMERCIAL COMPARISON

'FARROWCJPD' can be compared to the commercial cultivar *Camellia* 'Winter's Rose', unpatented. Plants of the new cultivar 'FARROWCJPD' are similar to plants of 'Winter's Rose' in most horticultural characteristics, however, plants of the new cultivar 'FARROWCJPD' differ in the following:

1. Plants of the new cultivar have a tighter, well-branched habit, while plants of this comparator have a looser, rangier habit.
2. Flowers and buds of the new cultivar are more abundant than flowers and buds of this comparator.
3. Foliage flush color of the new cultivar is burgundy-red, while the foliage flush color of this comparator is green.
4. Plants of the new cultivar are faster growing than plants of this comparator.

BRIEF DESCRIPTION OF THE PHOTOGRAPHS

The accompanying photograph in FIG. 1 illustrates in full color a plant of 'FARROWCJPD' grown outdoors in Grand Haven, Michigan, having the distinctive dark red flush.

Figure 1:
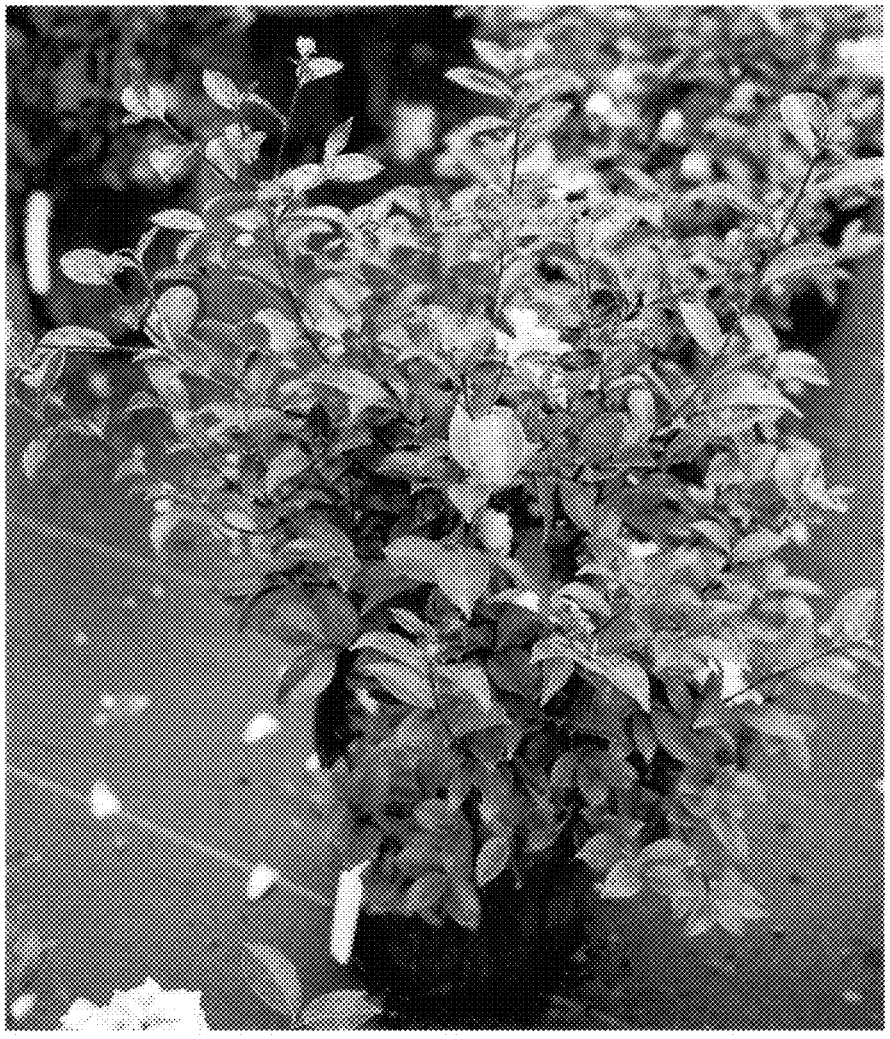
Figure 2:
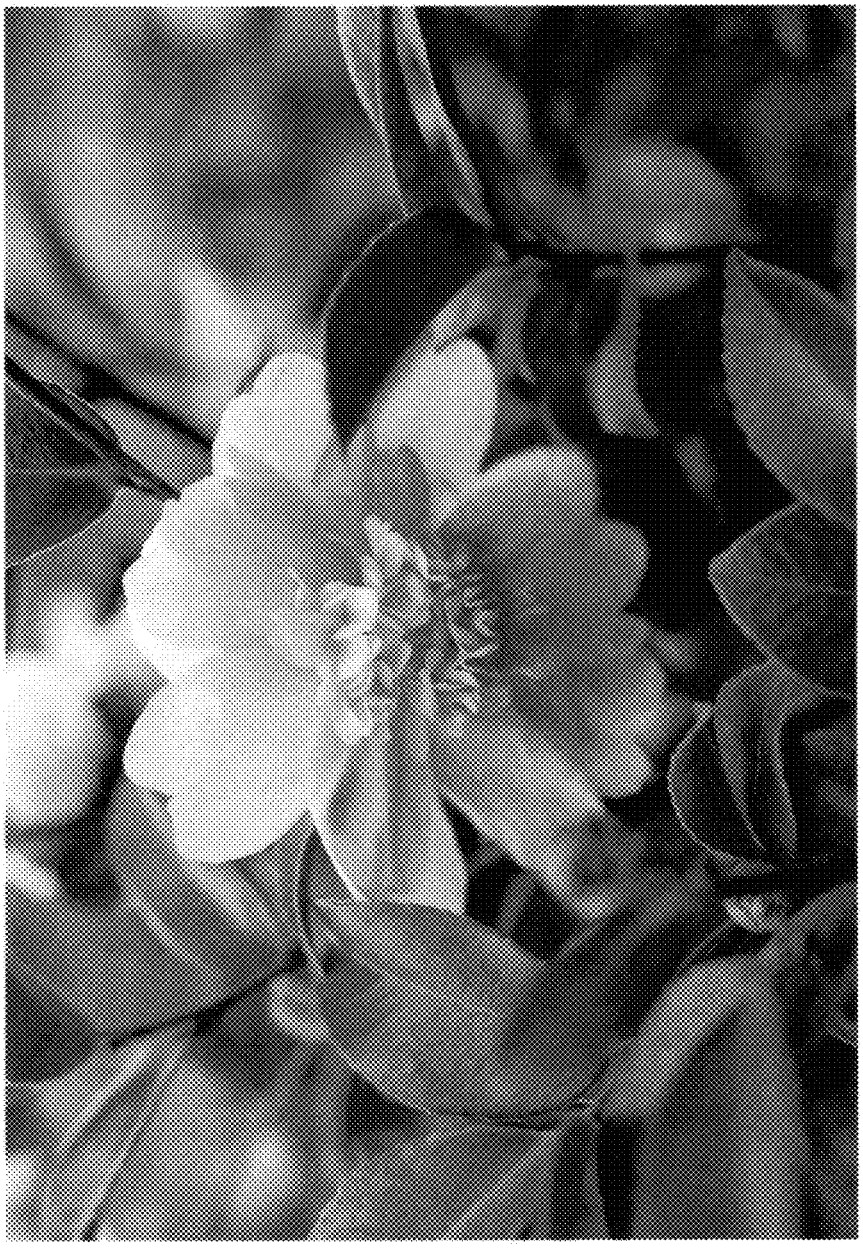
FIG. 2 shows a close-up view of a maturing flower of the new cultivar.
Figure 3:
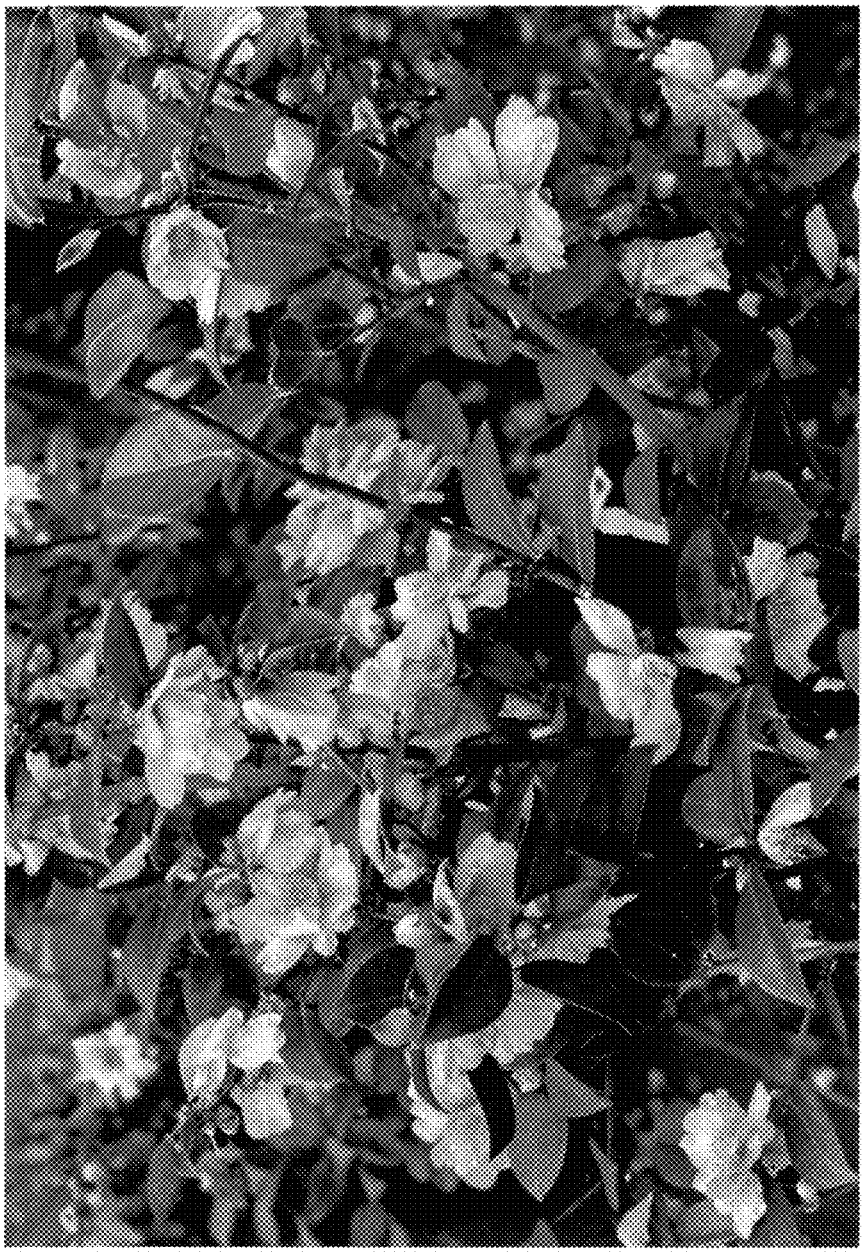
FIG. 3 illustrates a plant of the new cultivar in full bloom, with flowers fully open.

Plants photographed are approximately 3 to 4 years old. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'FARROWCJPD' plants grown in a poly-greenhouse in Grand Haven, Michigan in the fall of 2022. Plants are approximately 3 to 4 years old, in 3-gallon containers. The average day time temperature is 18-27° C., average night temperature is 5-10° C. Measurements and numerical values represent averages of typical plant types.

Botanical classification: *Camellia* hybrid 'FARROWCJPD'.

PROPAGATION

Method: Hardwood cuttings.
Time to rooting: 60 days in summer.
Time to produce rooted plant: 95 days in summer.
Root description: Moderately dense, freely branching, thin and fibrous. Off-white in color, not accurately measured by the color chart.

PLANT

Plant type: Perennial flowering shrub.
Plant shape: Upright.
Growth habit: Upwards and somewhat outwards.
Height: 90 cm.
Plant spread: 50 cm.
Growth rate: Moderate.
Branching characteristics:
- *Lateral branches.*—Branching Habit: Basal; some pinching required. Quantity: 3 to 4 main branches with approximately 20 branchlets each. Length: Main Branch: About 60 cm. Branchlet: About 20 cm. Diameter: 3 mm.
- *Stem.*—Shape: Rounded. Aspect: 45° to 90°. Strength: Strong. Texture: Fuzzy pubescence on new growth only. Older growth glabrous. Color: New Growth: RHS Greyed-Purple 183A. Old Growth: Between RHS Grey-Brown 199A and N199B.
- *Internode length.*—3 cm.

FOLIAGE

Leaf:
- *Type.*—Single.
- *Arrangement.*—Alternate.
- *Length.*—6 cm.
- *Width.*—2.5 cm.
- *Shape.*—Narrowly elliptic.
- *Apex.*—Acuminate.
- *Base.*—Attenuate.
- *Margin.*—Very slightly serrulate.
- *Texture of top surface.*—Glabrous, somewhat coriaceous.
- *Texture of bottom surface.*—Glabrous, somewhat coriaceous.
- *Color.*—Young foliage upper side: RHS Purple N77A. Young foliage under side: RHS Greyed-Orange 177A. Mature foliage upper side: RHS Green NN137A. Mature foliage under side: RHS Yellow-Green 147B.
- *Venation.*—Type: Pinnate. Venation color upper side: RHS Yellow-Green 147B. Venation color under side: RHS Yellow-Green 147B.

Petiole:
- *Length.*—5 mm.
- *Diameter.*—2 mm.
- *Texture, upper side.*—Slightly pubescent.
- *Texture, under side.*—Slightly pubescent.
- *Color, upper side.*—RHS Yellow-Green 147B.
- *Color, under side.*—RHS Yellow-Green 147B.

FLOWER

Bloom period: Fall.
Flowers:
- *Arrangement.*—Flowering at the terminal ends of lateral branches with buds typically emerging in pairs or groups of 3.
- *Shape.*—Double whorl.
- *Aspect.*—Outward.
- *Quantity of flowers per lateral stem.*—Approximately 5 per branchlet.
- *Quantity of buds per lateral stem.*—Approximately 5 per branchlet.
- *Quantity of flowers and buds per plant.*—About 100.
- *Length.*—7 cm.
- *Diameter.*—7 cm.
- *Depth.*—2.5 cm.
- *Persistence.*—Self-cleaning.
- *Fragrance.*—Mild to moderate intensity with notes of lemon peel and jasmine.

Petals:
- *Appearance.*—Delicate and soft with a feathery quality due to the presence of small furling petaloids.
- *Arrangement.*—Double whorl.
- *Length.*—Outer whorl: 4 cm. Inner whorl: 3.5 cm.
- *Width.*—Outer whorl: 2.5 cm. Inner whorl: 1.5 cm.
- *Apex.*—Outer whorl: Notched. Inner whorl: Notched.
- *Base.*—Outer whorl: Cuneate. Inner whorl: Attenuate.
- *Shape.*—Outer whorl: Elliptic to obovate. Inner whorl: Oblong.
- *Margin.*—Entire.
- *Number.*—About 20.
- *Fused.*—No.
- *Texture.*—Both sides soft and silky.
- *Color.*—Upper surface at first opening: RHS Red-Purple 64D. Under surface at first opening: RHS Red-Purple 64D. Upper surface at maturity: RHS Red-Purple 65B fading to 65A at the base. Under surface at maturity: RHS Red-Purple 65B fading to 65A at the base.

Petaloids:
- *Appearance.*—Emerging from partially transformed stamen filaments; irregularly shaped and furling.
- *Arrangement.*—Whorl.
- *Length.*—Average 3 cm.
- *Width.*—Average 0.5 cm.
- *Apex.*—Notched.

*Base*.—Attenuate, often fused to partially transformed stamen filaments.

*Shape*.—Oblong.

*Margin*.—Entire.

*Number*.—15 to 20.

*Fused*.—No.

*Texture*.—Both sides soft and silky.

*Color*.—Upper surface at first opening: RHS Red-Purple 64D. Under surface at first opening: RHS Red-Purple 64D. Upper surface at maturity: RHS Red-Purple 65B fading to 65A at the base. Under surface at maturity: RHS Red-Purple 65B fading to 65A at the base.

Bud:

*Shape*.—Ovoid.

*Length*.—1.5 cm.

*Diameter*.—1.25 cm.

*Color*.—RHS Green 143C.

Sepals: No sepals; calyx is shed upon bud break.

Peduncle:

*Length*.—2 mm.

*Diameter*.—2 mm.

*Color*.—RHS Yellow-Green 143C.

*Texture*.—Glabrous.

*Aspect*.—45° relative to stem.

*Strength*.—Strong.

REPRODUCTIVE ORGANS

Stamens:

*Number*.—About 60.

*Filament length*.—1.25 cm.

*Filament color*.—RHS Yellow 8B to 8C.

*Anthers*.—Length: 2 mm. Color: RHS Yellow 8B. Pollen: Quantity: Plentiful. Color: RHS Yellow 9A. Shape: Club-like.

Pistil:

*Number*.—1.

*Length*.—1 cm.

*Style*.—Length: 0.75 cm. Color: RHS Yellow-Green 145D.

*Stigma*.—Shape: Linear, split into 3. Color: RHS Yellow-Green 145D.

OTHER CHARACTERISTICS

Disease and pest resistance: Neither resistance nor susceptibility to normal pests of *Camellia* observed.

Temperature Tolerance: Tolerant to USDA 7 (6b)-9.

Fruit/seed: Not observed.

What is claimed is:

1. A new and distinct cultivar of *Camellia* plant named 'FARROWCJPD' as herein illustrated and described.

* * * * *